United States Patent [19]

Moss

[11] Patent Number: 5,085,661
[45] Date of Patent: Feb. 4, 1992

[54] SURGICAL FASTENER IMPLANTATION DEVICE

[76] Inventor: Gerald Moss, R.D.#1, West Sand Lake, N.Y. 12196

[21] Appl. No.: 605,270

[22] Filed: Oct. 29, 1990

[51] Int. Cl.⁵ .............................................. A61B 17/00
[52] U.S. Cl. .................................... 606/139; 606/144; 606/187
[58] Field of Search ............... 606/213, 216, 219, 139, 606/148, 144; 24/150

[56] References Cited

U.S. PATENT DOCUMENTS

| | | |
|---|---|---|
| 3,103,666 | 9/1963 | Bone . |
| 3,675,639 | 7/1972 | Cimber . |
| 3,875,648 | 4/1975 | Bone . |
| 3,910,281 | 10/1975 | Kletschka et al. . |
| 3,961,632 | 6/1976 | Moossun . |
| 4,006,747 | 2/1977 | Kronenthal et al. . |
| 4,126,124 | 11/1978 | Miller . |
| 4,144,876 | 3/1979 | Deleo . |
| 4,235,238 | 11/1980 | Ogiu et al. . |
| 4,669,473 | 6/1987 | Richards et al. . |
| 4,705,040 | 11/1987 | Mueller et al. . |

Primary Examiner—Stephen C. Pellegrino
Assistant Examiner—Gary Jackson
Attorney, Agent, or Firm—Schmeiser, Morelle & Watts

[57] ABSTRACT

A fastener implanting device used to implant a head portion of a "T" or "H"-shaped fastener within a body. The device has a needle portion and a grip portion. The needle portion has a fastener receiving cavity selectively covered by a movable sleeve. The sleeve's translational movement is controlled by a mechanism located in the device's grip portion.

14 Claims, 3 Drawing Sheets

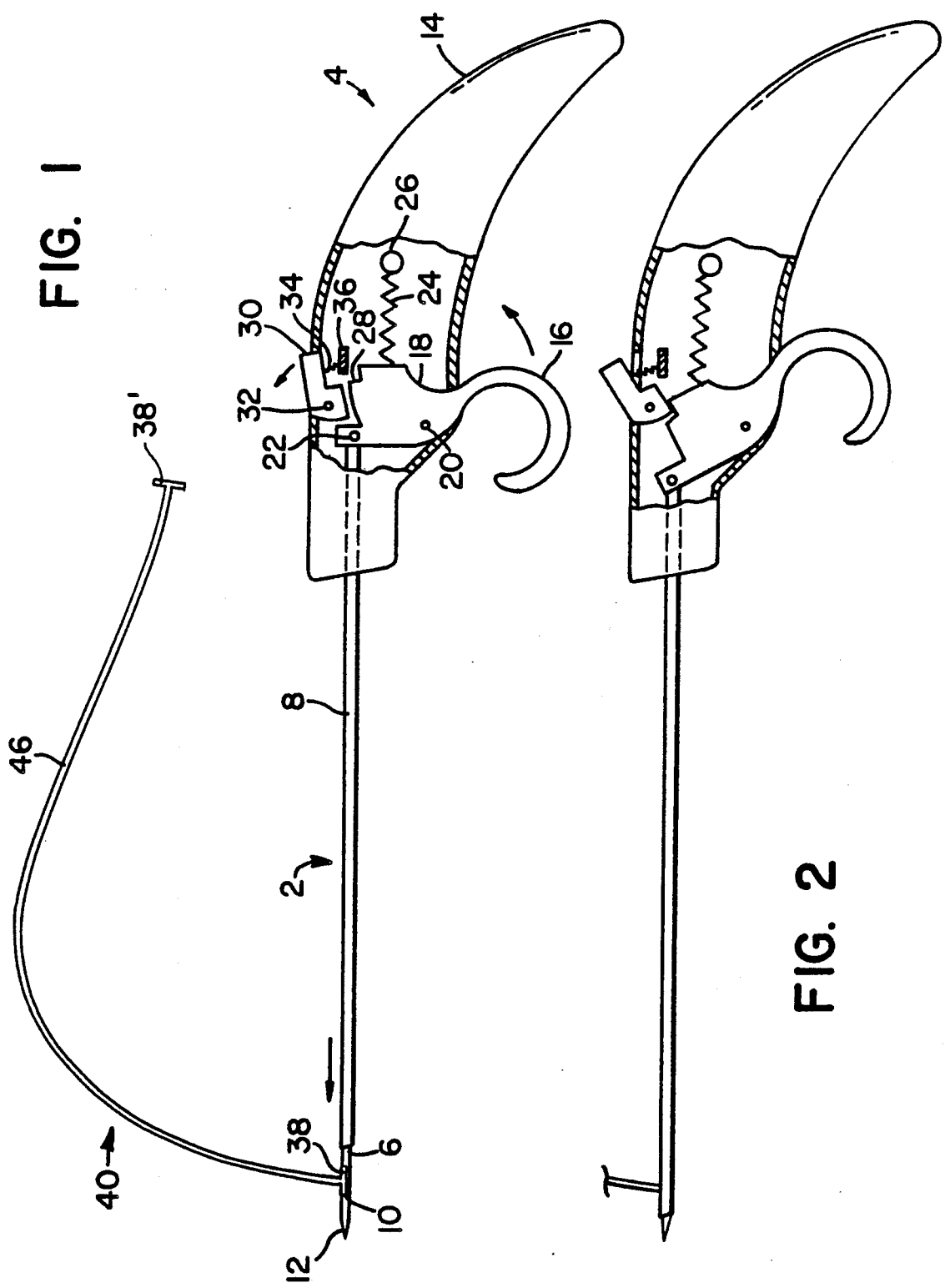

SURGICAL FASTENER IMPLANTATION DEVICE

FIELD OF THE INVENTION

The invention is in the field of surgical anchor devices. More particularly, the invention is used to implant and release a surgical anchor that is primarily used to secure a hollow organ to an outer tissue layer.

BACKGROUND OF THE INVENTION

Anchoring devices have been used in medicine for a number of years. Simple filament sutures (stitches) are used to hold one segment of tissue to another. With the advent of modern medicine, other types of anchors began to be used. To avoid the time required to sew up a wound and tie the sutures, rapid stapling procedures were developed. In the latter procedure, a form of staple is inserted into the tissue in lieu of a sewn stitch to hold the tissue segments together.

In 1977, Kronenthal et al received a patent (U.S. Pat. No. 4,006,747) on a new type of surgical fastening system. The system involves the partial insertion of "H"-shaped fasteners through the tissue adjacent an incision using a hollow needle and a push-rod. Once in place, an end of the fastener is located on each side of the incision and a filament that connects the two ends of the fastener consequently spans the incision. The fastener maintains the tissue in place thereby facilitating the natural healing process.

The "H" shaped fastener is also being used in a number of non-medically related fastening systems. This type of fastener is commonly used in stores to affix price tickets to clothing. A number of method are employed to install the fasteners in clothing. Two patents (U.S. Pat. Nos. 3,103,666 and 3,910,281) have been issued to A. R. Bone for hand held devices that aid in the insertion of this type of fastener into clothing.

In recent years, a modification of the fastening system has become prevalent in surgical procedures. Ogiu et al (U.S. Pat. No. 4,235,238), teaches a system wherein a "T" shaped fastener insertion needle is located within the end of an endoscope. Ogiu et al makes use of a hollow needle that has a longitudinally extending cavity sized to receive the head of the fastener. Once the needle has passed through the tissue on both sides of the wound, an obturator is pushed through the interior of the needle to dislodge the head of the fastener. The needle is then removed and an outer filament end of the fastener is tied to a lock member to maintain the closure of the wound.

Richards et al (U.S. Pat. No. 4,669,474) shows a similar system that makes use of a "T" shaped fastener. Richards et al implants the head of the fastener into the tissue using a hollow needle and push-rod (obturator). The head of the fastener is shaped so that it strongly anchors itself to the tissue and therefore provides a secure fastening point within the body. The filament end of the fastener is then secured exterior to the skin using a shaped retainer.

Mueller et al (U.S. Pat. No. 4,705,040) teaches a system that uses a "T" shaped fastener to anchor a hollow organ to the skin. In Mueller et al, a hollow needle and obturator are again used to implant the head of the fastener. However, Mueller et al places the head of the fastener within the interior cavity of the organ to be anchored. Mueller et al then makes use of a movable lock member to secure the outer filament end of the fastener to the exterior of the skin.

The presently used method and apparatus for inserting and placing "T"-shaped or "H"-shaped fasteners suffers from a number of deficiencies. Firstly, most of the prior art insertion needles have an open tip through which the head of the fastener is ejected. The hole in the needle's tip can catch and tear on the body tissue as the needle is pushed into the body. This can lead to a slower healing process and also possibly an increased chance of later infection. Secondly, when the obturator is pushed through the needle to eject the fastener, the doctor pushes on the obturator along its longitudinal axis while trying to hold the needle in place. Since this direction of force is also along the longitudinal axis of the hollow needle and the obturator is in contact with the needle, it is extremely difficult to eject the fastener without also moving the hollow needle. It is extremely easy to overcompensate for this inward force and accidentally pull the needle slightly outwards during the fastener ejection process. Thirdly, the insertion apparatus requires a significant amount of time to effect each fastener insertion. All of the above noted deficiencies combine to reduce the effectiveness and convenience of using "H"-shaped or "T"-shaped fasteners.

SUMMARY OF THE INVENTION

The invention is a fastener insertion device that can be used to quickly and accurately insert either a "T"-shaped or "H"-shaped fastener into a body. The invention employs a solid delivery needle that is attached to an ergonomically designed grip. Near the pointed end of the needle is a rectangularly shaped cavity sized to receive the cylindrical head of the fastener. Surrounding the major portion of the needle is a movable sleeve that includes a longitudinally extending slot located at its forward end. Located within the grip portion of the device is a mechanism that is used to selectively cause the sleeve to slide longitudinally on the needle. The grip portion includes a trigger shaped actuator and a position lock that can releasably lock the sleeve in its forward position.

An apparatus that is very similar to the invention is sold by the Anchor Products Company of Addison, Ill. Their product is called a "Soft Tissue Biopsy Device" and includes a similar handle and sleeved needle. Within the handle is a mechanism for moving the sleeve on the needle that is basically identical to that of the instant invention. However, the invention differs from the biopsy device both in function and design. The design differences include the shape of the needle tip, the shape of the needle cavity, the shape of the outer portion of the sleeve and the use of a slot in the outer end of the sleeve.

The invention is ideally suited for use in securing organs in place. In the preferred method of use, the doctor loads the head of the fastener into the end of the needle. He or she then pulls the trigger and thereby causes the sleeve to slide outwardly on the needle toward the needle's point. Once the sleeve is in its outward position, the lock secures the trigger and therefore the sleeve in place.

The slot on the outer end of the sleeve is located so that the end of the filament portion of the fastener fit through the slot. The portion of the sleeve surrounding the outer portions of the needle cavity releasably captures the head of the fastener between the inner surface of the sleeve and the inner surface of the cavity. Prior to insertion of the needle into the body tissue, the doctor pulls the loose end of the fastener's filament portion toward the handle portion of the device. This brings the filament in line with the needle body and produces a moment type force on the captured head portion of the fastener.

Next, the doctor inserts the needle portion of the device into the body at a location where the tip of the needle will extend into an organ cavity. He or she then unlocks the lock mechanism and this causes the trigger to move forwardly and the sleeve to move rearwardly on the needle into its "retracted" position. This uncovers the head of the fastener. Once the head is uncovered, the resilient action of the bent filament on the fastener head and also optionally pulling on the filament causes the fastener head to eject from the needle cavity. The doctor then removes the needle portion of the device from the body and "reloads" the needle with another fastener.

The instant invention requires no longitudinal forces to be applied to the device when ejecting the fastener. The device is easy to use and comfortable to handle due to its simple mechanism and shaped grip. A hole is not required in the front of the needle since the head of the fastener is ejected from the needle's side located cavity. In addition, unlike any of the prior art, a hollow needle is not required. A solid needle can be used since an obturator is not required for the ejection of the fastener head. A solid needle is stronger, easier to make and avoids the interior passage through which blood or infectious matter may pass.

BRIEF DESCRIPTION OF THE DRAWINGS

FIG. 1 shows the invention with the head portion of a fastener located within the needle cavity.

FIG. 2 shows the invention with the head portion of a fastener located within the needle cavity and secured by the sleeve.

DETAILED DESCRIPTION OF THE DRAWINGS

Figure 5:
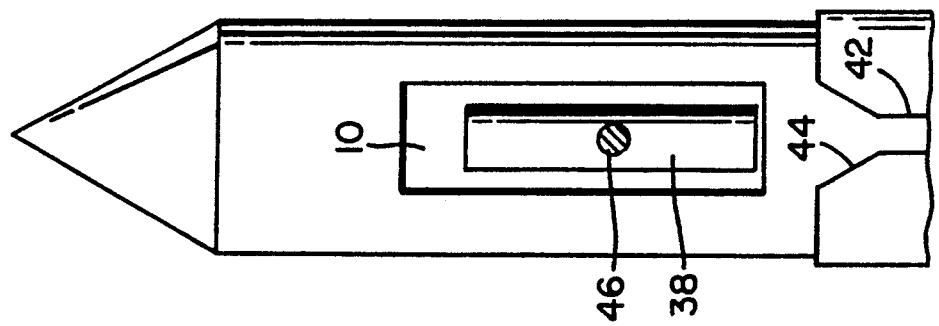
FIG. 5 shows a plan view of the needle end of the invention shown in FIG. 1.

Referring now to the drawings in greater detail, wherein like reference characters refer to like parts throughout the several figures, there is shown by the numeral 1 a fastener implanting device.

The device is comprised of an insertion portion 2 and a grip portion 4. The insertion portion basically includes a solid needle 6 and a slidable sleeve 8. The sleeve encircles the majority of the length of the needle and can be moved to selectively cover or expose a needle cavity 10 located proximate the tip 12 of the needle. The needle is preferably of 14 gauge and has a length of approximately six inches.

The grip portion 4 has a rearwardly extending handle portion 14 that is sized to securely fit within a user's clenched hand. Housed within the grip portion is a mechanism that enables the user to selectively cause the translation of the sleeve on the needle.

The translation system comprises a trigger 16 that is connected to a shaped rotary member 18. The trigger and rotary member pivot about a pivot pin 20. Rotatably received within the forward end of member 18 is a cylindrically shaped end portion 22 of the sleeve 8. The needle 6 is anchored to the forward end of the grip portion 16 by a conventional fastener such as a clamp and is not detailed.

A spring 24 is anchored to the housing at 26 and attached to the rotary member 18. The spring is used to provide a clockwise biasing of member 18. A top surface of member 18 includes a step 28 that can engage a lock member 30. The lock member pivots about a pin 32 and is in contact with a compression spring 34. The spring is anchored to the housing at 36 and provides a counterclockwise biasing of the lock member.

FIG. 1 shows the initial loading of the device. A cylindrically shaped head portion 38 of an "H"-shaped fastening member 40 is placed within the needle cavity 10. Once in place, the trigger is pulled rearwardly and this results in the device obtaining the configuration shown in FIG. 2.

FIG. 2 shows the device with the head of the fastener locked in place. As the trigger was moved rearwardly from the position shown in FIG. 1, the sleeve left its retracted position and moved outwardly on the needle. When the trigger is in its rearwardmost position, the end of the sleeve extends past the cavity 10 and the lock member 30 rotates in a counterclockwise direction due to its spring biasing and engages the trigger step 28. At this point, both the sleeve and the fastener are locked in place.

Figure 4:
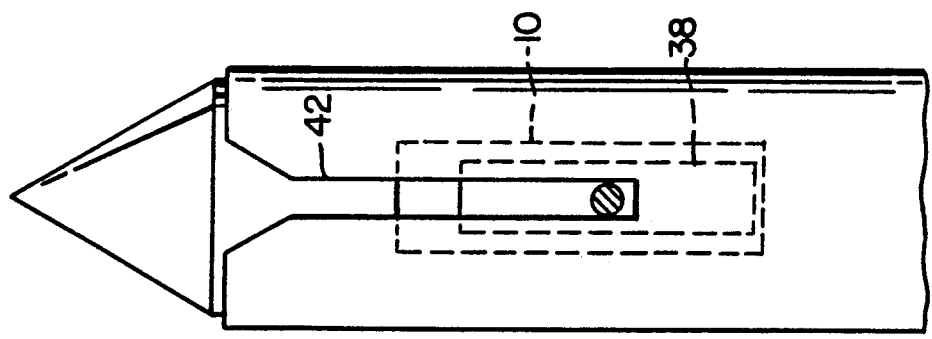
FIG. 4 shows a plan view of the needle end of the invention shown in FIG. 2.
Figure 3:
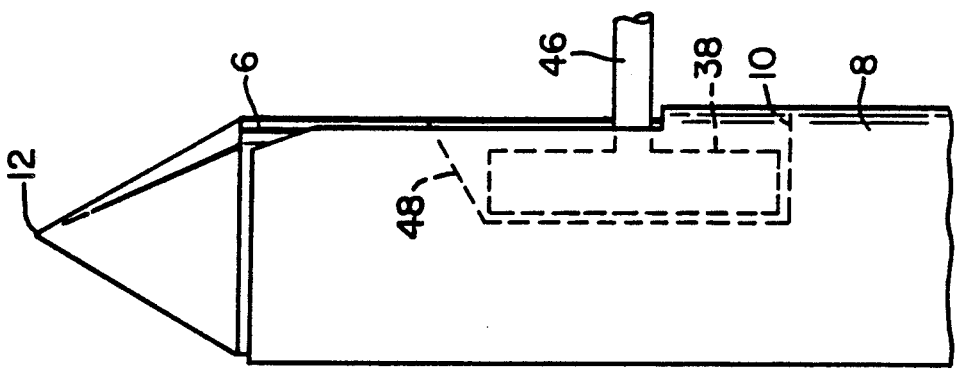
FIG. 3 shows a side view of the needle end of the invention shown in FIG. 2.

FIGS. 3 and 4 provide detailed views of the tip of the device shown in FIG. 2. As can be seen in these two figures, the end of the sleeve includes a slot 42 that has a rounded "V"-shaped entrance 44. The slot fits around the filament portion 46 of the fastener 40 adjacent the fastener's head 38. The needle itself has a sharp tip 12 that can be easily inserted through body tissue with a minimum of concomitant tearing of the tissue.

The cavity 10 is rectangular in shape and has an angled forward end 48. The cavity length is approximately 6-10 millimeters. The cavity has a width of approximately one-half to one millimeter. As shown, the cavity is sized to receive the head 38 of the fastener.

In FIGS. 4 and 5, the slot 42 in the sleeve can be easily seen. The filament portion 46 of the fastener extends outwardly through the slot. The slot is sized so that the sleeve can slide without the slot binding on the filament portion of the fastener. Another criterion of the slot is that its width must be less than the diameter of the head portion 38 of the fastener. This results in the portion of the sleeve adjacent the slot overlying a portion of the fastener head 38 and thereby locking it within the cavity until the sleeve is moved rearwardly.

Figure 6:
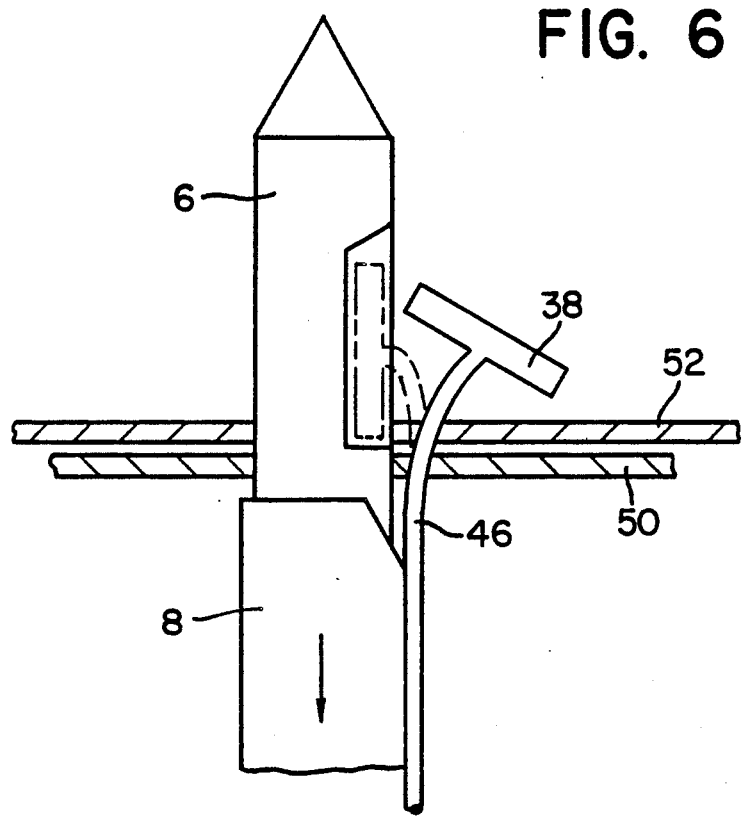
FIG. 6 shows the invention being used to implant the fastener within a hollow organ.

FIGS. 5 and 6 detail the forward portion of the insertion device when the sleeve has been moved to its rearward, retracted position. In FIG. 5, it can be seen that once moved rearwardly, the sleeve is completely withdrawn from above the cavity 10 thereby allowing the head 38 of the fastener to exit the cavity without interference. It should be noted that the sleeve is also in the retracted position when the head portion of the fastener is initially inserted into the needle cavity 10.

FIG. 6 shows the device being used to implant the head 38 of a fastener 40. As shown, the needle has been pushed past the outer skin layer 50 and into an organ cavity such as the interior of the stomach. The organ's outer surface is labeled 52. Once the device is properly positioned, the doctor releases lock 30 and the sleeve 8 moves rearwardly due to the action of spring 24. Without the sleeve holding the head of the fastener in place, the head portion of the fastener ejects from the needle cavity 10.

The fastener ejection process is accomplished by any of a number of different methods. The doctor can pull on the fastener's filament portion 46 and thereby cause the head 38 of the fastener to pull out of the needle cavity 10. A second method of release is based on the material used for the fastener. Preferably, the fastener is made from a semi-resilient plastic such as nylon or polypropylene. The filament 46 is joined to the cylindrically shaped head portion at a right angle to the head's longitudinal axis. When the fastener is first inserted into the body, the filament is pulled so that it lies adjacent the body of the needle/sleeve. This causes a moment type of force on the end of the fastener due to the approximately ninety degree bending of the filament end adjacent the head portion of the fastener (i.e.—the filament is caused to lie substantially parallel to the longitudinal axis of the fastener head). When the sleeve is later retracted, the restrained head will pop out of the cavity as the plastic filament returns to its unbent shape where it is perpendicular to the longitudinal axis of the fastener head. This effectively ejects the fastener's head from the needle cavity. This is shown in FIG. 6 in which the original placement of the fastener head is shown in phantom. Once the fastener is ejected, the needle is withdrawn.

Figure 7:
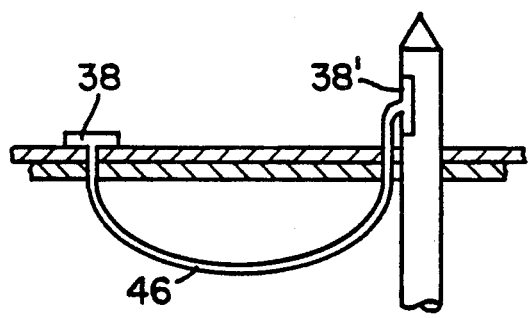
FIG. 7 shows a side view of the invention implanting a second end of an "H"-shaped fastener within a hollow organ.

FIG. 7 shows a second end of an "H"-shaped fastener being inserted into a hollow organ. As shown, one fastener head 38 has already been properly placed. The doctor has placed the second head portion 38' of the fastener into the device and inserted it into the body near the secured first end 38 of the fastener. Once the second end 38' of the fastener is in place, it is ejected from the needle cavity and the insertion device is removed.

Figure 8:
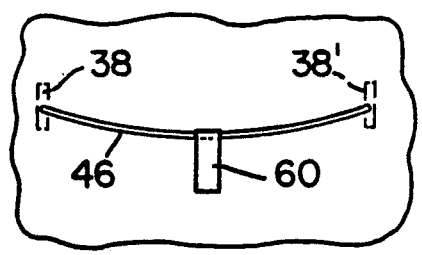
FIG. 8 shows a plan view of the body in the region shown in FIG. 7 with the filament of the fastener secured to the exterior of the skin.

Next, the filament 46 between the ends 38, 38' is secured. This is shown in FIG. 8. The figure shows an exterior view of the body in the region where the fastener heads have been inserted. The fastener's heads 38, 38' are shown in phantom. Once the fastener's head portions are secured, the doctor attaches a piece of tape 60 to the center portion of the filament 46. He or she then pulls the filament to the side until the proper tension is being applied to the fastener heads thereby anchoring the hollow organ to the skin. The doctor then applies the tape to the skin thereby temporarily securing the filament portion of the fastener. If the tension is later required to be adjusted, the tape is moved appropriately.

The above fastener securement method can also be used when a "T"-shaped fastener is inserted. The doctor merely ties the outer end of the fastener's filament portion to a piece of tape and applies the tape to the body in a location where the correct tension is applied.

The embodiment disclosed herein has been discussed for the purpose of familiarizing the reader with the novel aspects of the invention. Although a preferred embodiment of the invention has been shown and described, many changes, modifications and substitutions may be made by one having ordinary skill in the art without necessarily departing from the spirit and scope of the invention.

I claim:

1. In combination a fastener insertion device and shaped a fastener for insertion into a body, said fastener being of the type having an elongated head portion and a filament portion wherein said filament portion is attached to a center portion of said head portion, wherein said insertion device comprises:
   a needle means having a front pointed end and a longitudinal axis;
   a sleeve means movably located on said needle means;
   a sleeve translating means attached to said sleeve means and capable of moving said sleeve means on said needle means between a first position and a second position; and
   a fastener receiving means located on said needle means adjacent the pointed end of said needle whereby when said sleeve means is in said first position, said sleeve means is capable of maintaining a head portion of a fastener within said fastener receiving means and when said sleeve means is in said second position, a head portion of a fastener can be inserted into or ejected from the fastener receiving means.

2. The device of claim 1 further comprising a slot in said sleeve means wherein said slot is located so that when said sleeve means is in said first position with the head of a fastener located in the fastener receiving means; the filament portion of the fastener will pass through the slot in the sleeve means.

3. The device of claim 2 wherein the slot has a "V"-shaped entrance.

4. The device of claim 2 wherein the fastener receiving means in the needle means comprises a rectangular cavity in the needle.

5. The device of claim 4 wherein the rectangular cavity has a longitudinal axis and said cavity longitudinal axis is substantially parallel to the longitudinal axis of the needle means.

6. The device of claim 1 wherein the sleeve translating means is manually operable and comprises a trigger and a releasable trigger lock wherein moving the trigger from a first position to a second position causes said sleeve means to move from the sleeve means' first position to the sleeve means' second position and wherein said trigger lock locks said trigger in a position wherein said sleeve means is maintained in the sleeve means' first position.

7. The device of claim 1 further comprising a housing attached to a rear end of the needle and wherein at least a portion of the sleeve translating means is located within the housing.

8. The device of claim 7 wherein the housing has an ergonomically shaped grip portion.

9. The device of claim 1 further comprising a biasing means operatively connected to said sleeve means for biasing said sleeve means towards said second sleeve position.

10. A method for anchoring a hollow organ within a body comprising:
    placing a head portion of a fastener within a cavity located in a needle portion of an insertion device;

placing a sleeve portion of the insertion device at least partially over said needle cavity and thereby also securing the fastener head portion within said cavity;

inserting a portion of the needle within a hollow organ of a body to a point where the needle cavity is within said hollow organ;

changing the position of said sleeve portion so that said sleeve portion no longer secures the fastener head portion within said cavity;

removing the needle from the body; and pulling on a filament attached to said fastener head portion to thereby anchor said organ.

11. The method of claim 10 wherein the fastener filament is resilient and once the sleeve portion no longer secures the fastener head within the cavity, the resilient filament causes the fastener head to spring out of the cavity.

12. The method of claim 10 further comprising pulling on the filament attached to said fastener head immediately after said changing of the sleeve position to a position where it no longer secures said fastener head within said cavity.

13. A method for placing a portion of a fastener within a body comprising:

placing a head portion of a fastener within a cavity located within a needle that is a part of an insertion device;

placing a sleeve portion of the insertion device at least partially over said needle cavity and thereby securing the head portion of the fastener within said cavity;

inserting the needle through a quantity of body tissue;

moving said sleeve portion to a position where it no longer secures the head portion of the fastener within said cavity; and removing said needle from the body tissue.

14. The method of claim 13 wherein moving said sleeve portion over said needle cavity comprises moving an actuator that is attached to said sleeve in a direction away from a pointed end of said needle.

* * * * *